United States Patent
Du et al.

(10) Patent No.: US 10,888,506 B2
(45) Date of Patent: Jan. 12, 2021

(54) OIL-IN-WATER EMULSION COMPOSITION

(71) Applicant: L'OREAL, Paris (FR)

(72) Inventors: Yao Du, Kawasaki (JP); Kyoko Amazaki, Kawasaki (JP); Yasuko Harada, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/740,095

(22) PCT Filed: Aug. 17, 2016

(86) PCT No.: PCT/JP2016/074570
§ 371 (c)(1),
(2) Date: Dec. 27, 2017

(87) PCT Pub. No.: WO2017/030209
PCT Pub. Date: Feb. 23, 2017

(65) Prior Publication Data
US 2018/0185253 A1  Jul. 5, 2018

(30) Foreign Application Priority Data

Aug. 20, 2015 (JP) .................. 2015-162668

(51) Int. Cl.
| | | |
|---|---|---|
| A61K 8/06 | (2006.01) | |
| A61K 8/60 | (2006.01) | |
| A61K 8/73 | (2006.01) | |
| A61Q 17/04 | (2006.01) | |
| A61K 8/81 | (2006.01) | |
| A61Q 5/00 | (2006.01) | |

(52) U.S. Cl.
CPC .............. *A61K 8/062* (2013.01); *A61K 8/602* (2013.01); *A61K 8/73* (2013.01); *A61K 8/8158* (2013.01); *A61Q 5/00* (2013.01); *A61Q 17/04* (2013.01)

(58) Field of Classification Search
None
See application file for complete search history.

(56) References Cited

U.S. PATENT DOCUMENTS

| | | |
|---|---|---|
| 2,463,264 A | 3/1949 | Graenacher et al. |
| 5,624,663 A | 4/1997 | Deflandre et al. |

FOREIGN PATENT DOCUMENTS

| | | |
|---|---|---|
| CN | 101219093 A | 7/2008 |
| EP | 0 669 323 A1 | 8/1995 |
| EP | 1938784 A2 | 7/2008 |
| JP | 2005-511763 A | 4/2005 |
| JP | 2006-111627 A | 4/2006 |
| WO | 2009/080659 | 7/2009 |
| WO | 2009/080661 A2 | 7/2009 |
| WO | 2012/059348 A1 | 5/2012 |
| WO | 2014/083541 A2 | 6/2014 |
| WO | 2014/185317 A1 | 11/2014 |

OTHER PUBLICATIONS

International Search Report for PCT/JP2016/074570, dated Oct. 31, 2016.
Innisfree, "Daycream SPF 30 PA++," http://www.gnpd.com/sinatra/recordpage/2311736/?utm_source=download&utm_medium=rtf, Mintel GNPD, Apr. 2014, ID#2311736, [search date: Aug. 15, 2019], URL, https://www.gnpd.com/sinatra/recordpage/2311736/?utm_source=fed_search.
Dax Cosmetics, "Waterproof Sun Protection Cream SPF 50+," Mintel GNPD, Jul. 2015, ID#3303943, [search date: Aug. 15, 2019], URL, https://www.gnpd.com/sinatra/recordpage/3303943/?utm_source=fed_search.
Laboratoires Nigy, "Very High Protection Face Cream SPF 50+," Mintel GNPD, Apr. 2010, ID#1339173, [search date: Aug. 15, 2019], URL, https://www.gnpd.com/sinatra/recordpage/1339173/?utm_source=fed_search.
Japanese Office Action for counterpart Application No. 2015-162668, dated Aug. 26, 2019 with English Translation.
Chinese Office Action for counterpart Application No. 201680037904.9, dated Mar. 20, 2020 (Translated).

*Primary Examiner* — Robert A Wax
*Assistant Examiner* — Randeep Singh
(74) *Attorney, Agent, or Firm* — The Marbury Law Group, PLLC

(57) ABSTRACT

The present invention relates to a composition in the form of an O/W emulsion, comprising: (a) at least one UV filter; (b) at least one inulin or inulin modified with hydrophobic chains; (c) at least one sugar ether surfactant; (d) at least one hydrophilic acrylic polymer; and (e) water. The composition according to the present invention can provide a homogeneous film when being applied, and good cosmetic effects such as superior UV filtering effects, while providing a watery fresh feeling during the application and a non-sticky feeling after the application.

14 Claims, No Drawings

OIL-IN-WATER EMULSION COMPOSITION

CROSS REFERENCE TO RELATED APPLICATIONS

This is a national stage application of PCT/JP2016/074570, filed internationally on Aug. 17, 2016, which claims priority to Japanese Application No. 2015-162668, filed on Aug. 20, 2015, both of which are incorporated by reference herein in their entireties.

TECHNICAL FIELD

The present invention relates to a composition in the form of an oil-in-water (O/W) emulsion, more particularly to a cosmetic composition for making up and/or caring for the skin.

BACKGROUND ART

It is known practice, in the cosmetics or dermatological field, to use O/W emulsions. These emulsions which consist of a fatty phase dispersed in an aqueous phase have an external aqueous phase, and therefore cosmetic/dermatological products based on the O/W emulsions are pleasant to use due to the feeling of freshness that the external aqueous phase can provide.

WO2009/080659 discloses an O/W emulsion containing a hydrophobically modified inulin and at least one thickening polysaccharide of plant origin, which has good stability even without conventional surfactants such as polyglyceryl ester. Further, such an O/W emulsion brings good watery skin sensation and non-sticky after feel.

DISCLOSURE OF INVENTION

However, O/W emulsions including inulin or modified inulin tend to exhibit inhomogeneous spreading when being applied onto a substrate, in particular a keratin substance such as skin, due to insufficient affinity with the substrate, while providing a watery fresh feeling during the application and a non-sticky feeling after the application.

Therefore, it tends to be difficult for the O/W emulsions including inulin or modified inulin to form a homogeneous film. Thus, it is often difficult for cosmetic compositions based on O/W emulsions to provide good cosmetic effects such as superior UV filtering effects, if the O/W emulsions include a UV filter.

In order to cope with the above problem, a certain surfactant such as glyceryl stearate may be used in the O/W emulsion including inulin or modified inulin, and the surfactant may enhance affinity of the O/W emulsion with a substrate to facilitate making a more homogenous film on the substrate.

However, if such a surfactant is added to the O/W emulsion including inulin or modified inulin, the watery fresh feeling during the application and the non-sticky feeling after the application are lost.

An objective of the present invention is to provide a composition in the form of an O/W emulsion including inulin or modified inulin, which can provide a homogeneous film when being applied, which is preferable for good cosmetic effects such as superior UV filtering effects, while providing a watery fresh feeling during the application and a non-sticky feeling after the application.

The above objective can be achieved by a composition in the form of an O/W emulsion, comprising:

(a) at least one UV filter;
(b) at least one inulin or inulin modified with hydrophobic chains;
(c) at least one sugar ether surfactant;
(d) at least one hydrophilic acrylic polymer; and
(e) water.

The (a) UV filter may be selected from inorganic UV filters, organic UV filters, and mixtures thereof. The inorganic UV filter may be selected from the group consisting of metal oxides, and mixtures thereof. The organic UV filter may be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis (hydroxyphenylbenzotriazole) compounds; benzoxazole compounds; screening polymers and screening silicones; dimers derived from α-alkylstyrene; 4,4-diarylbutadiene compounds; and mixtures thereof.

The amount of the (a) UV filter in the composition may be from 0.01 to 30% by weight, preferably from 0.1 to 25% by weight, and more preferably from 5 to 20% by weight, relative to the total weight of the composition.

The hydrophobic chain in the (b) inulin modified with hydrophobic chains may be an alkylcarbamate group, preferably alkylcarbamate group of formula R—NH—CO— in which R is an alkyl group having 1 to 22 carbon atoms, and more preferably a laurylcarbamate group.

The amount of the (b) inulin or inulin modified with hydrophobic chains may be from 0.01 to 10% by weight, preferably from 0.1 to 5% by weight, and more preferably from 0.15 to 3% by weight, relative to the total weight of the composition.

The (c) sugar ether surfactant may be selected from glucoside type surfactants. The glucoside type surfactants may be represented by the following general formula:

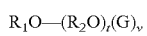

wherein
$R_1$ represents a hydrogen atom or a linear or branched alkyl radical containing from 1 to 30, preferably 6 to 28, and more preferably 8 to 26 carbon atoms, or an aralkyl radical containing from 7 to 30, preferably 7 to 28, and more preferably 7 to 26 carbon atoms, with the proviso that at least one of $R_1$ denotes a linear or branched alkyl radical containing from 1 to 30 carbon atoms;
$R_2$ represents an alkylene radical containing from 2 to 4 carbon atoms;
G represents a reduced sugar containing 5 or 6 carbon atoms;
t denotes a value ranging from 0 to 10; and
v denotes a value ranging from 1 to 15.

The amount of the (c) sugar ether surfactant may be from 0.01 to 20% by weight, preferably from 0.05 to 10% by weight, and more preferably from 0.1 to 5% by weight, relative to the total weight of the composition.

The (d) hydrophilic acrylic polymer may be acryloyldimethyl taurate polymer, preferably selected from the group consisting of sodium acrylate/sodium acryloyldimethyl taurate copolymer, acrylamide/sodium acryloyldimethyltaurate copolymer, ammonium polyacryloyldimethyl taurate, ammonium acryloyldimethyl taurate/VP copolymer, and combinations thereof.

The amount of the (d) hydrophilic acrylic polymer may be from 0.01 to 10% by weight, preferably from 0.05 to 5% by weight, and more preferably from 0.1 to 2% by weight, relative to the total weight of the composition.

The amount of the (e) water in the composition may be from 40 to 95% by weight, preferably from 50 to 90% by weight, and more preferably from 60 to 90% by weight, relative to the total weight of the composition.

The composition according to the present invention may further comprise (f) at least one fatty alcohol. Due to the presence of the (f) fatty alcohol, the UV filtering effects of the composition can be further enhanced.

The amount of the (f) fatty alcohol in the composition may be from 0.01 to 20% by weight, preferably from 0.05 to 10% by weight, and more preferably from 0.1 to 5% by weight, relative to the total weight of the composition.

The present invention also relates to a method of protecting a keratin substance from ultraviolet radiation comprising applying to the keratin substance the composition according to the present invention.

BEST MODE FOR CARRYING OUT THE INVENTION

After diligent research, the inventors have discovered that it is possible to provide a composition in the form of an O/W emulsion including inulin or modified inulin, which can provide a homogeneous film when being applied, and good cosmetic effects such as superior UV filtering effects, while providing a watery fresh feeling during the application and a non-sticky feeling after the application.

Thus, the composition according to the present invention is in the form of an O/W emulsion, and comprises:
(a) at least one UV filter;
(b) at least one inulin or inulin modified with hydrophobic chains;
(c) at least one sugar ether surfactant;
(d) at least one hydrophilic acrylic polymer; and
(e) water.

The term "O/W emulsion" or "oil-in-water emulsion" means any macroscopically homogeneous composition comprising a continuous aqueous phase and a fatty phase dispersed in the said aqueous phase in the form of droplets.

The composition according to the present invention can provide a homogeneous film, and can exhibit good cosmetic effects such as enhanced UV shielding effects, while providing a good feeling during use, such as a watery fresh feeling when being applied, and a non-sticky feeling after the application.

Hereafter, each of the compositions according to the present invention will be described in a detailed manner
[UV Filter]

The composition according to the present invention includes at least one (a) UV filter. If two or more (a) UV filters are used, they may be the same or different.

There is no limitation to the type of the UV filter. The UV filter can be selected from inorganic UV filters, organic UV filters, and mixtures thereof.

The amount of the (a) UV filter in the composition may be from 0.01 to 30% by weight, preferably from 0.1 to 25% by weight, and more preferably from 5 to 20% by weight, relative to the total weight of the composition.
(Inorganic UV Filter)

The composition according to the present invention may comprise at least one inorganic UV filter. If two or more inorganic UV filters are used, they may be the same or different, preferably the same.

The inorganic UV filter used for the present invention may be active in the UV-A and/or UV-B region. The inorganic UV filter may be hydrophilic and/or lipophilic. The inorganic UV filter is preferably insoluble in solvents such as water and ethanol commonly used in cosmetics.

It is preferable that the inorganic UV filter be in the form of a fine particle such that the mean (primary) particle diameter thereof ranges from 1 nm to 50 μm, preferably 5 nm to 500 nm, and more preferably 10 nm to 200 nm. The mean (primary) particle size or mean (primary) particle diameter here is an arithmetic mean diameter.

The inorganic UV filter can be selected from the group consisting of metal oxides which may or may not be coated, and mixtures thereof.

Preferably, the inorganic UV filter is selected from pigments (mean size of the primary particles: generally from 5 nm to 50 nm, preferably from 10 nm to 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. Preferably, the inorganic UV filter is selected from titanium oxide, zinc oxide, and more preferably titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes such as beeswax, (meth)acrylic polymers, organic UV filters, and (per)fluoro compounds.

It is preferable for the coating to include at least one organic UV filter. As the organic UV filter in the coating, a dibenzoylmethane derivative such as butyl methoxydibenzoylmethane (Avobenzone) and 2,2'-Methylenebis[6-(2H-Benzotriazol-2-yl)-4-(1,1,3,3-Tetramethyl-Butyl) Phenol] (Methylene Bis-Benzotriazolyl Tetramethylbutylphenol) marketed as "TINOSORB M" by BASF may be preferable.

In a known manner, the silicones in the coating(s) may be organosilicon polymers or oligomers comprising a linear or cyclic and branched or cross-linked structure, of variable molecular weight, obtained by polymerization and/or polycondensation of suitable functional silanes and essentially composed of repeated main units in which the silicon atoms are connected to one another via oxygen atoms (siloxane bond), optionally substituted hydrocarbon radicals being connected directly to said silicon atoms via a carbon atom.

The term "silicones" also encompasses silanes necessary for their preparation, in particular alkylsilanes.

The silicones used for the coating(s) can preferably be selected from the group consisting of alkylsilanes, polydialkylsiloxanes, and polyalkylhydrosiloxanes. More preferably still, the silicones are selected from the group consisting of octyltrimethylsilane, polydimethylsiloxanes, and polymethylhydrosiloxanes.

Of course, the inorganic UV filters made of metal oxides may, before their treatment with silicones, have been treated with other surfacing agents, in particular with cerium oxide, alumina, silica, aluminum compounds, silicon compounds, or their mixtures.

The coated inorganic UV filter may have been prepared by subjecting the inorganic UV filter to one or more surface treatments of a chemical, electronic, mechanochemical, and/ or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filters may be titanium oxides coated:

with silica, such as the product "Sunveil" from Ikeda, and "Sunsil TIN 50" from Sunjin Chemical;

with silica and with iron oxide, such as the product "Sunveil F" from Ikeda;

with silica and with alumina, such as the products "Microtitanium Dioxide MT 500 SA" from Tayca, "Tioveil" from Tioxide, and "Mirasun TiW 60" from Rhodia;

with alumina, such as the products "Tipaque TTO-55 (B)" and "Tipaque TTO-55 (A)" from Ishihara, and "UVT 14/4" from Kemira;

with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniquema, and the product "Eusolex T-AVO" from Merck;

with alumina and with aluminum laurate, such as the product "Microtitanium Dioxide MT 100 S" from Tayca;

with iron oxide and with iron stearate, such as the product "Microtitanium Dioxide MT 100 F" from Tayca;

with zinc oxide and with zinc stearate, such as the product "BR351" from Tayca;

with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca;

with silica, with alumina and with aluminum stearate and treated with a silicone, such as the product "STT-30-DS" from Titan Kogyo;

with silica and treated with a silicone, such as the product "UV-Titan X 195" from Kemira;

with alumina and treated with a silicone, such as the products "Tipaque TTO-55 (S)" from Ishihara or "UV Titan M 262" from Kemira;

with triethanolamine, such as the product "STT-65-S" from Titan Kogyo;

with stearic acid, such as the product "Tipaque TTO-55 (C)" from Ishihara; or with sodium hexametaphosphate, such as the product "Microtitanium Dioxide MT 150 W" from Tayca.

Other titanium oxide pigments treated with a silicone are preferably $TiO_2$ treated with octyltrimethylsilane and for which the mean size of the individual particles is from 25 and 40 nm, such as that marketed under the trademark "T 805" by Degussa Silices, $TiO_2$ treated with a polydimethylsiloxane and for which the mean size of the individual particles is 21 nm, such as that marketed under the trademark "70250 Cardre UF $TiO_2Si_3$" by Cardre, and anatase/rutile $TiO_2$ treated with a polydimethylhydrosiloxane and for which the mean size of the individual particles is 25 nm, such as that marketed under the trademark "Microtitanium Dioxide USP Grade Hydrophobic" by Color Techniques.

Preferably, the following coated $TiO_2$ can be used as the coated inorganic UV filter:

Stearic acid (and) Aluminum Hydroxide (and) $TiO_2$, such as the product "MT-100 TV" from Tayca, with a mean primary particle diameter of 15 nm;

Dimethicone (and) Stearic Acid (and) Aluminum Hydroxide (and) $TiO_2$, such as the product "SA-TTO-S4" from Miyoshi Kasei, with a mean primary particle diameter of 15 nm;

Silica (and) $TiO_2$, such as the product "MT-100 WP" from Tayca, with a mean primary particle diameter of 15 nm;

Dimethicone (and) Silica (and) Aluminum Hydroxide (and) $TiO_2$, such as the product "MT-Y02" and "MT-Y-110 M3S" from Tayca, with a mean primary particle diameter of 10 nm;

Dimethicone (and) Aluminum Hydroxide (and) $TiO_2$, such as the product "SA-TTO-53" from Miyoshi Kasei, with a mean primary particle diameter of 15 nm;

Dimethicone (and) Alumina (and) $TiO_2$, such as the product "UV TITAN M170" from Sachtleben, with a mean primary particle diameter of 15 nm; and Silica (and) Aluminum Hydroxide (and) Alginic Acid (and) $TiO_2$, such as the product "MT-100 AQ" from Tayca, with a mean primary particle diameter of 15 nm.

In terms of UV filtering ability, $TiO_2$ coated with at least one organic UV filter is more preferable. For example, Avobenzone (and) Stearic Acid (and) Aluminum Hydroxide (and) $TiO_2$, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ".

The uncoated zinc oxide pigments are, for example:
those marketed under the trademark "Z-cote" by Sunsmart;
those marketed under the trademark "Nanox" by Elementis; and
those marketed under the trademark "Nanogard WCD 2025" by Nanophase Technologies.

The coated zinc oxide pigments are, for example:
those marketed under the trademark "Oxide Zinc CS-5" by Toshiba (ZnO coated with polymethylhydrosiloxane);
those marketed under the trademark "Nanogard Zinc Oxide FN" by Nanophase Technologies (as a 40% dispersion in Finsolv TN, $C_{12}$-$C_{15}$ alkyl benzoate);
those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane);
those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane);
those marketed under the trademark "Escalol Z100" by ISP (alumina-treated ZnO dispersed in an ethylhexyl methoxycinnamate/PVP-hexadecene copolymer/methicone mixture);
those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in $C_{12}$-$C_{15}$ alkyl benzoate with hydroxystearic acid polycondensate).

The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220".

The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira.

Coated inorganic UV filters are preferable, because the UV filtering effects of the inorganic UV filters can be enhanced. In addition, the coating(s) may help uniformly or homogeneously disperse the UV filters in the composition according to the present invention.

(Organic UV Filter)

The composition according to the present invention may comprise at least one organic UV filter. If two or more organic UV filters are used, they may be the same or different, preferably the same.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof.

Anthranilic compounds: Methyl anthranilate, marketed under the trademark "Neo Heliopan MA" by Haarmann and Reimer.

Dibenzoylmethane compounds: Butyl methoxydibenzoylmethane, marketed in particular under the trademark "Parsol 1789" by Hoffinann-La Roche; and isopropyl dibenzoylmethane.

Cinnamic compounds: Ethylhexyl methoxycinnamate, marketed in particular under the trademark "Parsol MCX" by Hoffinann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomenthyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and ILA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by BASF, and ethylhexyl triazone marketed under the trademark «UVINUL T150» by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffinann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or "Mexoryl XL" by L'Oreal, as represented below.

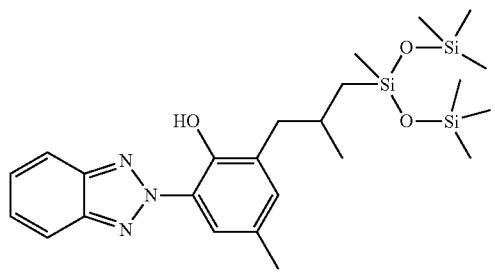 [SMILES: Cc1cc(CC(C)C[Si](C)(O[Si](C)(C)C)O[Si](C)(C)C)c(O)c(-n2nc3ccccc3n2)c1]

Benzoxazole compounds: 2,4-bis[5-1(dimethylpropyl) benzoxazol-2-yl-(4-phenyl)imino]-6-(2-ethylhexyl) imino-1,3,5-triazine, marketed under the trademark Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds: 1,1-dicarboxy(2,2'-dimethylpropyl)-4,4-diphenylbutadiene.

It is preferable that the organic UV filter(s) be selected from the group consisting of:
butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,1'-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy] disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl)imino-1,3,5-triazine, camphor benzylkonium methosulfate, and mixtures thereof.

[Inulin or Modified Inulin]

The composition according to the present invention includes at least one (b) inulin or inulin modified with hydrophobic chains. If two or more (b) inulin or inulin modified with hydrophobic chains are used, they may be the same or different.

Inulin belongs to the family of the fructans.

Fructans or fructosans are oligosaccharides or polysaccharides which comprise a sequence of anhydrofructose units optionally in combination with one or more saccharide residues other than fructose. Fructans may be linear or branched. Fructans may be products obtained directly from a plant or microbial source, or else products having a chain length which has been modified (increased or reduced) by fractionation, synthesis or hydrolysis, in particular enzymatically. Fructans generally have a degree of polymerization from 2 to approximately 1000, and preferably from 2 to approximately 60.

There are 3 distinct groups of fructans. The first group corresponds to products whose fructose units are for the most part bonded via P-2-1 bonds. These are essentially linear fructans such as inulins.

The second group also corresponds to linear fructoses, but the fructose units are essentially bonded via P-2-6 bonds. These products are levans.

The third group corresponds to mixed fructans, in other words those having β-2-6 and β-2-1 sequences. These are essentially branched fructans such as graminans.

Thus, inulin is one of polysaccharides, and a polymer of fructose Inulin may be obtained, for example, from endive, dahlia or Jerusalem artichoke. The inulin used in the composition according to the present invention is preferably obtained, for example, from endive.

The inulins used in the compositions according to the present invention may be hydrophobically modified. In particular they are obtained by grafting of hydrophobic chains onto the hydrophilic backbone of the fructan.

The hydrophobic chains which can be grafted onto the main chain of the fructan may in particular be linear or branched, saturated or unsaturated hydrocarbon chains having 1 to 50 carbon atoms, preferably 8 to 22 carbon atoms, such as alkyl, arylalkyl, alkylaryl and alkylene groups, divalent cycloaliphatic groups, or organopolysiloxane chains. These hydrocarbon or organopolysiloxane chains may in particular comprise one or more ester, amide, urethane, carbamate, thiocarbamate, urea, thiourea and/or sulphonamide functions, such as, in particular, methylenedicyclohexyl and isophorone, or divalent aromatic groups such as phenylene.

A "hydrophobically modified inulin" according to the present invention is in particular an inulin modified with hydrophobic chains, especially an inulin modified by the grafting of hydrophobic chains onto the hydrophilic backbone of said inulin.

In particular, the hydrophobically modified inulin exhibits a degree of polymerization from 2 to approximately 1000 and preferably from 2 to approximately 60, and a degree of substitution of less than 2 on the basis of one fructose unit.

According to a preferred embodiment, the hydrophobic chains have at least one alkylcarbamate group of formula R—NH—CO— in which R is an alkyl group having 1 to 22 carbon atoms, preferably 8 to 16 carbon atoms.

According to a more preferred embodiment the hydrophobic chains are laurylcarbamate groups.

In particular, illustrative and non-limitative instances of hydrophobically modified inulins that can be used in the compositions according to the present invention include stearoyl inulin, such as those sold under the names Lifidrem INST by Engelhard and Rheopearl INS by Ciba; palmitoyl inulin; undecylenoyl inulin, such as those sold under the names Lifidrem INUK and Lifidrem INUM by Engelhard; and inulin laurylcarbamate, such as that sold under the name Inutec SP1 by Beneo and Inutec SL1 by Creachem.

Use is made in particular of a grafted inulin laurylcarbamate, resulting in particular from the reaction of lauryl isocyanate with an inulin, especially an inulin obtained from endive. Examples of these compounds include, in particular, the product sold under the name Inutec SP1 by Beneo and Inutec SL1 by Creachem.

The amount of the (b) inulin or inulin modified with hydrophobic chains may be from 0.01 to 10% by weight, preferably from 0.1 to 5% by weight, and more preferably from 0.15 to 3% by weight, relative to the total weight of the composition.

[Sugar Ether Surfactant]

The composition according to the present invention comprises at least one (c) sugar ether surfactant. If two or more (c) sugar ether surfactants are used, they may be the same or different.

The (c) sugar ether surfactant is a surfactant which has at least one sugar moiety and at least one ether bond. It is preferable that the (c) sugar ether surfactant be selected from glucoside type surfactants.

The glucoside type surfactant may preferably be selected from the group consisting of alkyl glucosides and alkyl polyglucosides.

The glucoside type surfactant may be represented by the following general formula:

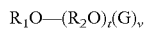

wherein
$R_1$ represents a hydrogen atom or a linear or branched alkyl radical containing from 1 to 30, preferably 6 to 28, and more preferably 8 to 26 carbon atoms, or an aralkyl radical containing from 7 to 30, preferably 7 to 28, and more preferably 7 to 26 carbon atoms, with the proviso that at least one of $R_1$ denotes a linear or branched alkyl radical containing from 1 to 30 carbon atoms;
$R_2$ represents an alkylene radical containing from 2 to 4 carbon atoms;
G represents a reduced sugar containing 5 or 6 carbon atoms;
t denotes a value ranging from 0 to 10; and
v denotes a value ranging from 1 to 15.

The reduced sugar containing 5 or 6 carbon atoms represented by G in the above formula may be selected from the group consisting of glucose, fructose and galactose.

The glucoside type surfactant may preferably be selected from the group consisting of caprylyl/capryl glucoside, decyl glucoside, lauryl glucoside, cetearyl glucoside, arachidyl glucoside, isostearyl glucoside, oleyl glucoside, C12-20 alkyl glucoside, and mixtures thereof.

Examples of the glucoside type surfactant that may be mentioned include decylglucoside (alkyl-$C_9$/$C_{11}$-polyglucoside (1.4)), for instance the product sold under the name Mydol 10 by the company Kao Chemicals, the product sold under the name Plantaren 2000 UP and Plantacare 2000 UP by the company BASF, and the product sold under the name Oramix NS10 by the company SEPPIC; caprylyl/capryl glucoside, for instance the product sold under the name Oramix CG110 by the company SEPPIC or under the name Lutensol GD70 by the company BASF; laurylglucoside, for instance the products sold under the names Plantaren 1200 N and Plantacare 1200 by the company Henkel; cocoglucoside, for instance the product sold under the name Plantacare 818/UP by the company Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of a mixture of arachidyl and behenyl alcohols and arachidyl glucoside marketed under the name MONTANOV 202 by Seppic, cocoylethylglucoside, for example in the form of a mixture (35/65) with cetyl and stearyl alcohols, marketed under the name MONTANOV 82 by Seppic, C12-20 alkyl glucoside, for example, in the form of a mixture with C14-22 alcohols, marketed under the name MONTANOV L by Seppic, and mixtures thereof.

The amount of the (c) sugar ether surfactant may be from 0.01 to 20% by weight, preferably from 0.05 to 10% by weight, and more preferably from 0.1 to 5% by weight, relative to the total weight of the composition.

[Hydrophilic Acrylic Polymer]

The composition according to the present invention comprises at least one (d) hydrophilic acrylic polymer. If two or more (d) hydrophilic acrylic polymers are used, they may be the same or different.

The (d) hydrophilic acrylic polymer can function as a thickener.

According to the present invention, the term "hydrophilic acrylic polymers" means non-hydrophobic and non-amphiphilic acrylic polymers.

Said hydrophilic acrylic polymers according to the present invention are either polyacrylamidomethylpropanesulfonic acid (AMPS) acrylic polymers or acrylic acid polymers.

Among the hydrophilic acrylic polymers that may be mentioned are the following polymers.

1) Acrylic Polymers Comprising at Least One Monomer Bearing a Sulfonic Group

According to a first embodiment, the hydrophilic acrylic polymer used according to the present invention comprises at least one monomer bearing a sulfonic group.

The polymers used in accordance with the present invention are homopolymers that may be obtained from at least one ethylenically unsaturated monomer bearing a sulfonic group, which may be in free form or partially or totally neutralized form.

Preferentially, the polymers in accordance with the present invention are partially or totally neutralized with a mineral base (sodium hydroxide, potassium hydroxide or aqueous ammonia) or an organic base such as monoethanolamine, diethanolamine, triethanolamine, an aminomethylpropanediol, N-methylglucamine, basic amino acids, for instance arginine and lysine, and mixtures of these compounds. They are generally neutralized.

In the present invention, the term "neutralized" means polymers that are totally or virtually totally neutralized, i.e. at least 90% neutralized.

The polymers used in the composition of the present invention generally have a number-average molecular weight ranging from 1000 to 20 000 000 g/mol, preferably ranging from 20 000 to 5 000 000 g/mol and even more preferentially from 100 000 to 1 500 000 g/mol.

These polymers according to the present invention may be crosslinked or noncrosslinked.

The monomers bearing a sulfonic group of the polymer used in the composition of the present invention are especially chosen from vinylsulfonic acid, styrenesulfonic acid, (meth)acrylamido($C_1$-$C_{22}$)alkylsulfonic acids, N—($C_1$-$C_{22}$) alkyl(meth)acrylamido($C_1$-$C_{22}$)alkylsulfonic acids such as undecylacrylamidomethanesulfonic acid, and also partially or totally neutralized forms thereof, and mixtures thereof.

According to one preferred embodiment of the present invention, the monomers bearing a sulfonic group are chosen from (meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, 2-methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid and 2-acrylamido-2, 6-dimethyl-3-heptanesulfonic acid, and also partially or totally neutralized forms thereof, and mixtures thereof.

More particularly, 2-acrylamido-2-methylpropanesulfonic acid (AMPS), and also partially or totally neutralized forms thereof, are used.

When the polymers are crosslinked, the crosslinking agents may be chosen from the polyolefinically unsaturated compounds commonly used for crosslinking polymers obtained by free-radical polymerization.

Examples of crosslinking agents that may be mentioned include divinylbenzene, diallyl ether, dipropylene glycol diallyl ether, polyglycol diallyl ether, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also the allylic esters of phosphoric and/or vinylphosphonic acid derivatives, or mixtures of these compounds.

According to one preferred embodiment of the present invention, the crosslinking agent is chosen from methylenebisacrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The homopolymer of monomers bearing a sulfonic group may be crosslinked with one or more crosslinking agents.

These homopolymers are generally crosslinked and neutralized, and they may be obtained according to the preparation process comprising the following steps:
(a) the monomer such as 2-acrylamido-2-methylpropanesulfonic acid in free form is dispersed or dissolved in a solution of tert-butanol or of water and tert-butanol;
(b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%;
(c) the crosslinking monomer(s) are added to the solution or dispersion obtained in (b);
(d) a standard free-radical polymerization is performed in the presence of free-radical initiators at a temperature ranging from 10 to 150° C.; the polymer precipitates in the tert-butanol-based solution or dispersion.

The preferred AMPS homopolymers are generally characterized in that they comprise, randomly distributed:
a) from 90% to 99.9% by weight of units of general formula (II) below:

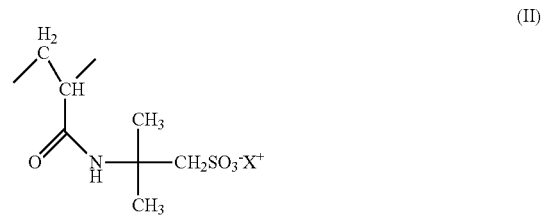

(II)

in which $X^+$ denotes a proton, an alkali metal cation, an alkaline-earth metal cation or the ammonium ion, not more than 10 mol % of the cations $X^+$ possibly being protons $H^+$;
b) from 0.01% to 10% by weight of crosslinking units derived from at least one monomer containing at least two olefinic double bonds; the weight proportions being defined relative to the total weight of the polymer.

The homopolymers according to the present invention that are more particularly preferred comprise from 98% to 99.5% by weight of units of formula (II) and from 0.2% to 2% by weight of crosslinking units.

A polymer of this type that may especially be mentioned is the crosslinked and neutralized 2-acrylamido-2-methylpropanesulfonic acid homopolymer sold by the company Clariant under the trade name Hostacerin AMPS (CTFA name: ammonium polyacryldimethyltauramide) or Simulgel 800 (CTFA name: ammonium polyacryloyldimethyl taurate) sold by the company Seppic.

As other acrylic polymers comprising at least one monomer bearing a sulfonic group, mention may especially be made of acryloyldimethyltaurate polymer, preferably acryloyldimethyltaurate copolymer. Acryloyldimethyltaurate polymer is a polymer comprising acryloyldimethyltaurate as a monomer, and acryloyldimethyltaurate copolymer is a copolymer comprising acryloyldimethyltaurate as a monomer and one or more other monomers. As acryloyldimethyltaurate copolymer, mention may be made of a copolymer of acryloyldimethyltaurate, and vinylpyrrolidone (VP) such as ammonium acryloyldimethyl taurate/VP copolymer, sold under the name Aristoflex AVC from Clariant.

2) Acrylamide/AMPS Copolymers

According to another embodiment, the hydrophilic acrylic polymer is a crosslinked anionic copolymer formed from units derived from the reaction between (i) acrylamide (monomer 1), (ii) 2-acrylamido-2-methylpropanesulfonic acid (monomer 2, referred to hereinbelow for convenience as AMPS) and (iii) at least one polyolefinically unsaturated compound (monomer 3), constituting here the crosslinking agent.

The crosslinked anionic copolymers used in the context of the present invention are products that are already known per se and their preparation has been described especially in patent application. EP-A-0 503 853, the content of which is consequently included in its entirety by reference in the present description.

The above copolymers may thus be obtained conventionally according to the emulsion polymerization technique from three different co-monomers included in their constitution.

The polyolefinically unsaturated monomers used as crosslinking agents for the preparation of the copolymers in accordance with the present invention are preferably chosen from the group formed by methylenebisacrylamide, allyl sucrose and pentaerythritol. Even more preferentially, use is made of methylenebisacrylamide.

Preferably, said polyolefinically unsaturated compound is present in the copolymer in a concentration of between 0.06 and 1 mmol per mole of the monomer units as a whole.

The ratio, expressed in mol %, between acrylamide and AMPS is preferentially between 85/15 and 15/85, advantageously between 70/30 and 30/70, even more preferentially between 65/35 and 35/65 and even more particularly between 60/40 and 40/60. In addition, AMPS is generally at least partially neutralized in the form of a salt, for example with sodium hydroxide, with potassium hydroxide or with a low molecular weight amine such as triethanolamine, or mixtures thereof.

A crosslinked copolymer that is particularly preferred in the context of the implementation of the present invention corresponds to the one prepared in Example 1 of patent application EP-A-0 503 853 mentioned above, and which is then in the form of a water-in-oil inverse emulsion. More precisely, this copolymer is formed from 60 mol % of acrylamide and 40 mol % of the sodium salt of AMPS, and it is crosslinked with methylenebisacrylamide in a proportion of 0.22 mmol per mole of the total monomer mixture. The final water-in-oil inverse emulsion preferably contains about 40% by weight of crosslinked copolymer as defined above and about 4% by weight of an ethoxylated fatty alcohol with an HLB of about 12.5.

Crosslinked copolymers that are more particularly used according to the present invention are the products sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) sold by the company SEPPIC, or Simulgel EG (C11-A name: sodium acrylate/sodium acryloyldimethyltaurate copolymer/isohexadecane/polysorbate 80).

3) Other Hydrophilic Acrylic Polymers

As other hydrophilic acrylic polymers that may be used according to the present invention, mention may also be made of:

homopolymers or copolymers of acrylic or methacrylic acids or salts thereof and esters thereof, such as the products sold under the names Carbopol 934, 940, 954, 981 and 980 by the company Noveon, Synthalen L® from the company 3V, sodium polymethacrylate sold under the name Darvan No. 7® by the company Vanderbilt, the products sold under the names Versicol F or Versicol K by the company Allied Colloid, Ultrahold 8 by the company Ciba Geigy and polyacrylic acids of Synthalen K type, polyacrylates and polymethacrylates such as glyceryl acrylate polymers, and in particular copolymers of glyceryl acrylate and of acrylic acid, such as the products sold under the names Lubrajel® MS, Lubrajel® CG, Lubrajel® DV, Lubrajel® NP, Lubrajel® OIL Lubrajel® Oil BG, Lubrajel® PF, Lubrajel® TW and Lubrajel® WA by the company Guardian Laboratories. Use is preferably made of Lubrajel MS, polyacrylic acid/alkyl acrylate copolymers of Pemulen type, copolymers of acrylic acid salt/vinyl alcohol, such as the product sold under the name Hydragen FN® from Cognis, and mixtures thereof.

It may be preferable that the (d) hydrophilic acrylic polymer be acryloyldimethyl taurate polymer, more preferably be selected from the group consisting of sodium acrylate/sodium acryloyldimethyl taurate copolymer, acrylamide/sodium acryloyldimethyltaurate copolymer, ammonium polyacryloyldimethyl taurate, ammonium acryloyldimethyl taurate/VP copolymer, and combinations thereof.

The amount of the (d) hydrophilic acrylic polymer may be from 0.01 to 10% by weight, preferably from 0.05 to 5% by weight, and more preferably from 0.1 to 2% by weight, relative to the total weight of the composition.

[Fatty Alcohol]

The composition according to the present invention may comprise at least one (f) fatty alcohol. If two or more (d) fatty alcohols are used, they may be the same or different.

The term "fatty" here means the inclusion of a relatively large number of carbon atoms. Thus, alcohols which have 4 or more, preferably 6 or more, and more preferably 8 or more carbon atoms are encompassed within the scope of fatty alcohols. The fatty alcohols may be saturated or unsaturated. The fatty alcohol may be linear or branched.

The fatty alcohol may have the structure R—OH wherein R is chosen from saturated and unsaturated, linear and branched radicals containing from 8 to 40 carbon atoms, such as from 8 to 30 carbon atoms.

In at least one embodiment, R is chosen from $C_{12}$-$C_{24}$ alkyl and $C_{12}$-$C_{24}$ alkenyl groups. R may be or may not be substituted with at least one hydroxyl group.

Non-limiting examples of fatty alcohols that may be mentioned include lauryl alcohol, cetyl alcohol, stearyl alcohol, oleyl alcohol, behenyl alcohol, linoleyl alcohol, undecylenyl alcohol, palmitoleyl alcohol, arachidonyl alcohol, arachidyl alcohol, erucyl alcohol, cetearyl alcohol, C14-22 alcohols, and mixtures thereof.

Examples of suitable fatty alcohols include, but are not limited to, stearyl alcohol, behenyl alcohol, arachidyl alcohol, C14-C22 alcohols, and mixtures thereof.

The fatty alcohol may be or may not be oxyalkylenated or glycerolated. Preferably, the fatty alcohol is not be oxyalkylenated or glycerolated As used herein, the term "oxyalkylenated fatty alcohol" is understood to mean any pure fatty alcohol with the following structure:

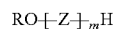

in which:

R is chosen from saturated or unsaturated, linear or branched radicals comprising from 8 to 40 carbon atoms, for example, from 8 to 30 carbon atoms, Z is an oxyethylene radical of formula (i) and/or an oxypropylene radical chosen from oxypropylene radicals of formulas $(ii)_1$ and $(ii)_2$:

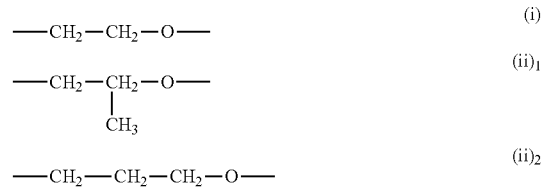

m is the number of ethylene oxide groups and/or propylene oxide groups, and may range from 1 to 250, for example, from 2 to 100.

As used herein, the term "glycerolated fatty alcohol" is understood to mean any pure fatty alcohol with the following structure:

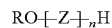

in which:
R is chosen from saturated or unsaturated, linear or branched radicals comprising from 8 to 40 carbon atoms, for example, from 8 to 30 carbon atoms,
Z is a glycerol radical of formula (iii):

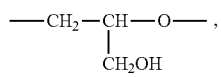

and
n is the number of glycerol groups, and may range from 1 to 30, for example, from 1 to 10.

In at least one embodiment of the present invention, the oxyalkylenated fatty alcohols used in accordance with the disclosure may be chosen from saturated or unsaturated, linear or branched fatty alcohols comprising from 10 to 20 carbon atoms and from 2 to 40 ethylene oxide groups.

Non-limiting examples of oxyalkylenated fatty alcohols include the following commercial products:
MERGITAL LM2 (Cognis) [lauryl alcohol 2 EO];
IFRALAN L12 (Ifrachem) and REWOPAL 12 (Goldschmidt) [lauryl alcohol 12 EO];
EMPILAN KA 2.5/90 FL (Albright & Wilson) and MERGITAL BL309 (Cognis) [decyl alcohol 3 EO];
EMPILAN KA 5/90 FL (Albright & Wilson) and MERGITAL BL589 (Cognis) [decyl alcohol 5 EO];
BRIJ 58 (Uniquema) and SIMULSOL 58 (Seppic) [cetyl alcohol 20 EO];
EMULGIN 05 (Cognis) [oleyl/cetyl alcohol 5 EO];
MERGITAL OC30 (Cognis) [oleyl/cetyl alcohol 30 EO];
BRIJ 72 (Uniquema) [stearyl alcohol 2 EO];
BRIJ 76 (Uniquema) [stearyl alcohol 10 EO];
BRIJ 78P (Uniquema) [stearyl alcohol 20 EO];
BRIJ 700 (Uniquema) [stearyl alcohol 100 EU];
EMULGIN B1 (Cognis) [cetearyl alcohol 12 EU];
EMULGIN L (Cognis) [cetyl alcohol 9 EU and 2 PO]; and
WITCONOL APM (Goldschmidt) [myristyl alcohol 3 PO].

Examples of glycerolated fatty alcohols include, but are not limited to, lauryl alcohol comprising 4 mol of glycerol (INCI name: polyglyceryl-4 lauryl ether), oleyl alcohol comprising 4 mol of glycerol (INCI name: polyglyceryl-4 oleyl ether), oleyl alcohol comprising 2 mol of glycerol (INCI name: polyglyceryl-2 oleyl ether), cetearyl alcohol comprising 2 mol of glycerol, cetearyl alcohol comprising 6 mol of glycerol, oleyl/cetyl alcohol comprising 6 mol of glycerol, and octadecanol comprising 6 mol of glycerol.

The amount of the (f) fatty alcohol in the composition may be from 0.01 to 20% by weight, preferably from 0.05 to 10% by weight, and more preferably from 0.1 to 5% by weight, relative to the total weight of the composition.

[Oil]

The composition according to the present invention may comprise at least one oil. If two or more oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The oil may be a non-polar oil such as a hydrocarbon oil, a silicone oil, or the like; a polar oil such as a plant or animal oil and an ester oil or an ether oil; or a mixture thereof.

The oil may be selected from the group consisting of oils of plant or animal origin, synthetic oils, silicone oils, and hydrocarbon oils.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used according to the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

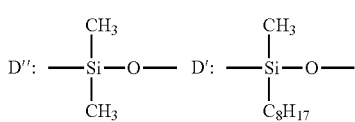

with $$D'': \ \begin{array}{c} CH_3 \\ | \\ -Si-O- \\ | \\ CH_3 \end{array} \quad D': \ \begin{array}{c} CH_3 \\ | \\ -Si-O- \\ | \\ C_8H_{17} \end{array}$$

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

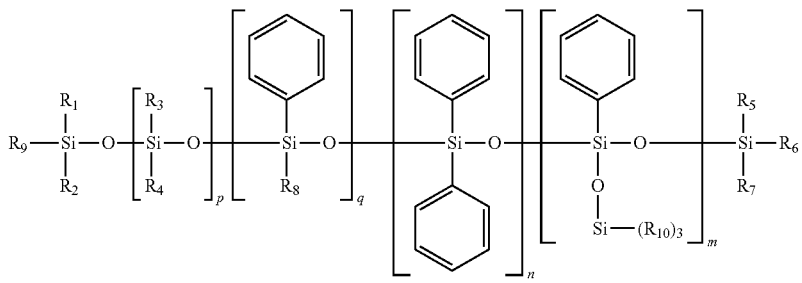

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl or butyl radicals, and m, n, p and q are, independently of each other, integers 0 to 900 inclusive, preferably 0 to 500 inclusive, and more preferably 0 to 100 inclusive, with the proviso that the sum n+m+q is other than 0.

Examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1154, SF 1250 and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and
linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

It is preferable that the oil be chosen from ester oils such as diisopropyl sebacate.

The amount of the oil in the composition according to the present invention may range from 0.1 to 20% by weight, preferably from 0.5 to 15% by weight, and more preferably from 1 to 10% by weight, relative to the total weight of the composition.

Due to the presence of oily UV filter, and possibly with at least one oil, the composition according to the present invention also comprises at least one fatty phase.

Since the composition according to the present invention is in the form of an O/W emulsion, the fatty phase in the composition according to the present invention can be the dispersed as inner phases in the O/W emulsion.

The amount of the fatty phase in the composition according to the present invention is 40% by weight or less, preferably 35% by weight or less, more preferably 30% by weight or less, and even more preferably 25% by weight or less, relative to the total weight of the composition.

On the other hand, the amount of the fatty phase in the composition according to the present invention may be 1% by weight or more, preferably 5% by weight or more, and more preferably 10% by weight or more, relative to the total weight of the composition.

Thus, for example, the amount of the fatty phase may be from 1 to 40% by weight, preferably from 5% to 35% by weight, more preferably from 10% to 30% by weight, and even more preferably from 15% to 25% by weight, in relation to the total weight of the composition.

[Other Ingredients]

The composition according to the present invention may also comprise at least one additional ingredient.

The amount of the additional ingredient(s) is not limited, but may be from 0.1 to 30% by weight relative to the total weight of the composition according to the present invention. The additional ingredient(s) may be selected from the group consisting of anionic, cationic, nonionic or amphoteric polymers; anionic, cationic or amphoteric surfactants; peptides and derivatives thereof; protein hydrolyzates; swelling agents and penetrating agents; agents for combating hair loss; anti-dandruff agents; natural or synthetic thickeners for oils except for the ingredient (a); suspending agents; sequestering agents; opacifying agents; dyes; sunscreen agents; vitamins or provitamins; fragrances; preserving agents, stabilizers; and mixtures thereof.

The vehicle for the composition according to the present invention is preferably an aqueous medium consisting of water and may advantageously contain one or several cosmetically acceptable organic solvents, which particularly include alcohols, such as butylene glycol, ethylene glycol, ethyl alcohol, isopropyl alcohol, benzyl alcohol and phenylethyl alcohol, or polyols or polyol ethers, such as ethylene glycol monomethyl, monoethyl and monobutyl ethers, propylene glycol or ethers thereof, such as propylene glycol monomethylether, butylene glycol, dipropylene glycol as well as diethylene glycol alkyl ethers, such as diethylene glycol monoethylether or monobutylether and glycerol.

The amount of the (d) water in the composition may be from 40 to 95% by weight, preferably from 50 to 90% by weight, and more preferably from 60 to 90% by weight, relative to the total weight of the composition.

The organic solvent(s) may then be present in a concentration of from 0.1 to 20% by weight, and preferably from 1 to 10% by weight relative to the total weight of the composition.

[Cosmetic Use]

The composition according to the present invention may preferably be used as a cosmetic composition. In particular, the composition according to the present invention may be intended for application onto a keratin substance such as skin, scalp and/or lips, preferably the skin. Thus, the composition according to the present invention can be used for a cosmetic process for the skin. The compositions according to the present invention can further constitute a composition intended for absorbing ultraviolet light, and/or for protecting a keratin substance especially of human from ultraviolet radiation. It is well known in the art that protection of the keratin substance from ultraviolet radiation results in anti-ageing, anti-wrinkle, and moisturizing. Accordingly, the composition of the present invention can further constitute a composition intended for ant-aging, anti-wrinkle and/or moisturizing.

The cosmetic process or cosmetic use for a keratin substance such as skin, according to the present invention comprises, at least, the step of applying onto the keratin substance the composition according to the present invention. The present invention can also relates to a method of protecting a keratin substance from ultraviolet radiation comprising applying to the keratin substance the composition according to the present invention, as well as a method of absorbing ultraviolet light comprising applying the composition according to the present invention and subjecting the keratin substance to ultraviolet light. These methods can be defined as non-therapeutic methods,

EXAMPLES

The present invention will be described in a more detailed manner by way of examples. However, these examples should not be construed as limiting the scope of the present invention. The examples below are presented as non-limiting illustrations in the field of the present invention.

Examples 1-3 and Comparative Examples 1-4

The following compositions according to Examples 1-3 and Comparative Examples 1-4, shown in Table 1, were prepared by mixing the ingredients shown in Table 1. The numerical values for the amounts of the ingredients shown in Table 1 are all based on "% by weight" as active raw materials.

TABLE 1

|  |  | Ex. 1 | Ex. 2 | Ex. 3 | Comp. Ex. 1 | Comp. Ex. 2 | Comp. Ex. 3 | Comp. Ex. 4 |
|---|---|---|---|---|---|---|---|---|
| Water | | q.s. 100 | q.s. 100 | q.s. 100 | q.s. 100 | q.s. 100 | q.s. 100 | q.s. 100 |
| Propylene Glycol | | 2 | 2 | 2 | 2 | 2 | 2 | 2 |
| Phenoxyethanol | | 0.4 | 0.4 | 0.4 | 0.4 | 0.4 | 0.4 | 0.4 |
| Disodium EDTA | | 0.1 | 0.1 | 0.1 | 0.1 | 0.1 | 0.1 | 0.1 |
| Inulin Lauryl Carbamate (INUTEC SL1 by Creachem) | | 0.25 | 0.25 | 0.25 | 0.25 | 0.25 | 0.25 | 0.25 |
| Decyl Glucoside (PLANTACARE 2000 UP by BASF) | | 1 | — | 1 | — | — | — | — |
| C12-20 Alkyl Glucoside (MONTANOV L by SEPPIC) | | — | 0.2 | — | — | — | — | 0.2 |
| Glyceryl Stearate (and) PEG-100 Stearate (SIMULSOL 165 by SEPPIC) | | — | — | — | — | — | 1 | — |
| C14-22 Alcohols | | — | 0.8 | — | — | — | — | 0.8 |
| Behenyl Alcohol 77%, Arachidyl Alcohol 18%, Stearyl Alcohol 5% (LANETTE 22, by BASF) | | — | — | 1 | — | 1 | — | — |
| Diisopropyl Sebacate | | 5 | 5 | 5 | 5 | 5 | 5 | 5 |
| Ethylhexyl Methoxycinnamate | | 6.5 | 6.5 | 6.5 | 6.5 | 6.5 | 6.5 | 6.5 |
| Drometrizole Trisiloxane | | 3 | 3 | 3 | 3 | 3 | 3 | 3 |
| Bis-Ethylhexyloxyphenol Methoxyphenyl Triazine | | 3 | 3 | 3 | 3 | 3 | 3 | 3 |
| Titanium Dioxide (and) Aluminum Hydroxide (and) Stearic Acid (MICRO TITANIUM DIOXIDE MT-100 T V by Tyca) | | 2.5 | 2.5 | 2.5 | 2.5 | 2.5 | 2.5 | 2.5 |
| Xanthan Gum | | 0.1 | 0.1 | 0.1 | 0.1 | 0.1 | 0.1 | 0.5 |
| Ammonium Acryloyldimethyltaurate/VP Copolymer (ARISTOFLEX AVC by Clariant) | | 0.4 | 0.4 | 0.4 | 0.4 | 0.4 | 0.4 | — |
| Alcohol Denat. | | 5 | 5 | 5 | 5 | 5 | 5 | 5 |
| Film Homogeneity (Score) | | 4.5 | 4 | 5 | 2.5 | 3 | 3 | 3 |
| SPF in vitro (Labsphere 2000) | | 22 | 24 | 47 | 13 | 16 | 18 | 24.5 |
| Sensory Evaluation | Watery Fresh Sensation | Good | Good | Good | Good | Good | Poor | Good |
| | Stickiness | Good | Good | Good | Good | Good | Poor | Poor |

[Evaluations]

The compositions according to Examples 1-3 and Comparative Examples 1-4 were evaluated as follows.

(Film Homogeneity)

Each of the compositions according to Examples 1-3 and Comparative Examples 1-4 was applied on a polypropylene sheet by an applicator to prepare samples with a film on the sheet. The thickness of the film was 10 μm. 3 samples were prepared for each of the compositions according to Examples 1-3 and Comparative Examples 1-4.

Then, each of the samples was exposed to a UV lamp (UV black ray B-100AP: Wavelength 365 nm). The samples with a good film homogeneity exhibited homogeneous black color. On the other hand, the samples with a poor film homogeneity exhibited non-homogeneous black color, and rather exhibited a translucent blue color.

Pictures of the samples exposed with UV rays were taken, and scored from 1 to 5 (1 is low film homogeneity, and 5 is high film homogeneity). The average score for the compositions according to Examples 1-3 and Comparative Examples 1-4 were calculated. The results are shown in Table 1.

(SPF In Vitro)

The sun protection factor (SPF) was determined according to the "in vitro" method described by B. L. Diffey in J.

Soc. Cosmet. Chem. 40, 127-133, (1989). The measurements were made using a UV-2000 spectrophotometer from the company Labsphere. Each of the compositions according to Examples 1-3 and Comparative Examples 1-4 was applied to on a PMMA plate in an amount of 1 mg/cm². The SPF in vitro value was calculated by UV2000. The results are shown in Table 1.

(Sensory Evaluation)

The watery fresh sensation during application of the compositions according to Examples 1-3 and Comparative Examples 1-4 to the skin was evaluated by applying each of the compositions to a forearm at a rate of 2 mg/cm², and then assessing the friction force felt between the fingers and the surface of the forearm to evaluate stickiness, in accordance with the following criteria Watery Fresh Feeling:
Good: Watery Fresh Feeling
Poor: No Watery Fresh Feeling
Stickiness:
Good: Less Sticky
Poor: Sticky The results are shown in Table 1.

It is clear from Table 1 that a combination of the sugar ether surfactant and the hydrophilic acrylic polymer can contribute to providing a homogeneous film when being applied, and superior UV filtering effects, while providing a watery fresh feeling during the application and a non-sticky feeling after the application.

It is also clear from Table 1 that the addition of a fatty alcohol can further enhance UV filtering effects.

Example 4

The following composition was prepared by mixing the ingredients shown in Table 2. The numerical values for the amounts of the ingredients shown in Table 2 are all based on "% by weight" as active raw materials.

TABLE 2

| | |
|---|---|
| WATER | q.s. 100 |
| GLYCERIN | 4 |
| PROPYLENE GLYCOL | 3.6 |
| POTASSIUM CETYL PHOSPHATE | 1 |
| DISODIUM EDTA | 0.1 |
| INULIN LAURYL CARBAMATE (INUTEC SL1 by Creachem) | 0.1 |
| TEREPHTHALYLIDENE DICAMPHOR SULFONIC ACID | 4 |
| DISODIUM STEAROYL GLUTAMATE | 0.2 |
| SODIUM METHYL STEAROYL TAURATE | 0.2 |
| STEARIC ACID | 2 |
| C12-20 ALKYL GLUCOSIDE (MONTANOV L by SEPPIC) | 0.3 |
| C14-22 ALCOHOLS | 1.2 |
| BIS-ETHYLHEXYLOXYPHENOL METHOXYPHENYL TRIAZINE | 1 |
| ETHYLHEXYL METHOXYCINNAMATE | 7 |
| DROMETRIZOLE TRISILOXANE | 4 |
| TITANIUM DIOXIDE (and) ALUMINUM HYDROXIDE (and) STEARIC ACID (MICRO TITANIUM DIOXIDE MT-100 T V by Tyca) | 2 |
| DIMETHICONE | 4 |
| CARBOMER | 0.2 |
| AMMONIUM ACRYLOYLDIMETHYLTAURATE/VP COPOLYMER (ARISTOFLEX AVC by Clariant) | 0.4 |
| NYLON-12 | 1 |
| PHENOXYETHANOL | 0.5 |
| TOCOPHEROL | 0.25 |
| FRAGRANCE | 0.2 |
| ALCOHOL DENAT. | 3 |
| TRIETHANOLAMINE | 2 |

The invention claimed is:

1. A composition in the form of an oil-in-water emulsion, comprising:
   (a) at least one UV filter;
   (b) at least one inulin, optionally modified with hydrophobic chains;
   (c) at least one sugar ether surfactant;
   (d) at least one hydrophilic acrylic polymer selected from the group consisting of sodium acrylate/sodium acryloyldimethyl taurate copolymer, acrylamide/sodium acryloyldimethyltaurate copolymer, ammonium polyacryloyldimethyl taurate, ammonium acryloyldimethyl taurate/VP copolymer, or combinations thereof; and
   (e) water,
   wherein:
      the at least one UV filter is present in the composition in an amount ranging from about 0.01% to about 30% by weight, relative to the total weight of the composition;
      the at least one inulin is present in an amount ranging from about 0.01% to about 10% by weight, relative to the total weight of the composition;
      the at least one sugar ether surfactant is present in an amount ranging from about 0.05% to about 10% by weight, relative to the total weight of the composition;
      the at least one hydrophilic acrylic polymer is present in an amount ranging from about 0.01% to about 10% by weight, relative to the total weight of the composition; and
      the water is present in an amount ranging from about 40% to about 95% by weight, relative to the total weight of the composition.

2. The composition according to claim 1, wherein the at least one UV filter is selected from inorganic UV filters, organic UV filters, or mixtures thereof.

3. The composition according to claim 2, wherein the inorganic UV filters are selected from metal oxides, or mixtures thereof, and wherein the organic UV filters are selected from anthranilic compounds, dibenzoylmethane compounds, cinnamic compounds, salicylic compounds, camphor compounds, benzophenone compounds, β, β-diphenylacrylate compounds, triazine compounds, benzotriazole compounds, benzalmalonate compounds, benzimidazole compounds, imidazoline compounds, bis-benzoazolyl compounds, p-aminobenzoic acid (PABA) compounds, methylenebis(hydroxyphenylbenzotriazole) compounds, benzoxazole compounds, screening polymers and screening silicones, dimers derived from α-alkylstyrene, 4,4-diarylbutadienes compounds, or mixtures thereof.

4. The composition according to claim 1, wherein the at least one UV filter is present in the composition in an amount ranging from about 0.1% to about 25% by weight, relative to the total weight of the composition.

5. The composition according to claim 1, wherein the inulin is modified with hydrophobic chains, and wherein the hydrophobic chain is an alkylcarbamate group.

6. The composition according to claim 1, wherein the at least one inulin is present in an amount ranging from about 0.1% to about 5% by weight, relative to the total weight of the composition.

7. The composition according to claim 1, wherein the at least one sugar ether surfactant is selected from glucoside type surfactants.

8. The composition according to claim 7, wherein the glucoside type surfactant is chosen from compounds according to the formula below:

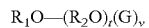

wherein:
- R$_1$ is chosen from a hydrogen atom or a linear or branched alkyl radical containing from 1 to 30 carbon atoms, or an aralkyl radical containing from 7 to 30 carbon atoms, with the proviso that at least one R$_1$ is a linear or branched alkyl radical containing from 1 to 30 carbon atoms;
- R$_2$ is an alkylene radical containing from 2 to 4 carbon atoms;
- G is a reduced sugar containing 5 or 6 carbon atoms;
- t is a value ranging from 0 to 10; and
- v is a value ranging from 1 to 15.

9. The composition according to claim 1 wherein the at least one sugar ether surfactant is present in an amount ranging from about 0.1% to about 5% by weight, relative to the total weight of the composition.

10. The composition according to claim 1, wherein the at least one hydrophilic acrylic polymer is present in an amount ranging from about 0.05% to about 5% by weight, relative to the total weight of the composition.

11. The composition according to claim 1, wherein the water is present in an amount ranging from about 50% to about 90% by weight, relative to the total weight of the composition.

12. The composition according to claim 1, further comprising at least one fatty alcohol.

13. The composition according to claim 12, wherein the at least one fatty alcohol is present in an amount ranging from about 0.01% to about 20% by weight, relative to the total weight of the composition.

14. A method of protecting a keratin substance from ultraviolet radiation comprising applying to the keratin substance a composition in the form of an oil-in-water emulsion, comprising:

(a) at least one UV filter;
(b) at least one inulin, optionally modified with hydrophobic chains;
(c) at least one sugar ether surfactant;
(d) at least one hydrophilic acrylic polymer selected from the group consisting of sodium acrylate/sodium acryloyldimethyl taurate copolymer, acrylamide/sodium acryloyldimethyltaurate copolymer, ammonium polyacryloyldimethyl taurate, ammonium acryloyldimethyl taurate/VP copolymer, or combinations thereof; and
(e) water, wherein:
- the at least one UV filter is present in the composition in an amount ranging from about 0.01% to about 30% by weight, relative to the total weight of the composition;
- the at least one inulin is present in an amount ranging from about 0.01% to about 10% by weight, relative to the total weight of the composition;
- the at least one sugar ether surfactant is present in an amount ranging from about 0.05% to about 10% by weight, relative to the total weight of the composition;
- the at least one hydrophilic acrylic polymer is present in an amount ranging from about 0.01% to about 10% by weight, relative to the total weight of the composition; and
- the water is present in an amount ranging from about 40% to about 95% by weight, relative to the total weight of the composition.

* * * * *